United States Patent [19]

Komatsu et al.

[11] 4,069,266
[45] Jan. 17, 1978

[54] PROCESS FOR THE PREPARATION OF FLUORINE-RICH ORGANIC COMPOUNDS CONTAINING ONE OR TWO CARBON ATOMS

[75] Inventors: Tadaaki Komatsu, Saitama; Hirokazu Takeda, Kamifukuoka; Hideki Oshio; Kimiaki Matsuoka, both of Kawagoe; Minoru Aramaki, Ube, all of Japan

[73] Assignee: Central Glass Company, Limited, Ube, Japan

[21] Appl. No.: 762,339

[22] Filed: Jan. 25, 1977

[30] Foreign Application Priority Data

Jan. 26, 1976 Japan .................................. 51-6630

[51] Int. Cl.$^2$ ............................................. C07C 17/20
[52] U.S. Cl. ..................................................... 260/653
[58] Field of Search ........................................ 260/653

[56] References Cited

U.S. PATENT DOCUMENTS 3,087,974  4/1963  Hauptschein et al. ............... 260/653
3,651,156  3/1972  Scherer et al. ...................... 260/653

FOREIGN PATENT DOCUMENTS 19,568/67  10/1967  Japan .................................. 260/653
19,445/67   9/1967  Japan .................................. 260/653

*Primary Examiner*—C. Davis
*Attorney, Agent, or Firm*—Fleit & Jacobson

[57] ABSTRACT

A process for preparing fluorine-rich organic compounds containing one or two carbon atoms from organic fluoro compounds of lower fluorine content in which starting partially or completely halogenated fluoro carbon compounds having at least one halogen atom other than fluorine, e.g., $CHCl_2F$, $CHClF_2$, $CCl_2F_2$, $CCl_3F$, $C_2Cl_3F_3$, $C_2Cl_2F_4$ and $C_2Cl_4F_2$, are contacted under disproportionation conditions with a catalyst system of a specific type which comprises 0.1 – 5% by weight, as metal, of a nickel(II) halide, titanium(III) chloride or titanium(III) fluoride and a balance of an aluminum compound such as activated alumina, silica, alumina or aluminum fluoride.

7 Claims, No Drawings

PROCESS FOR THE PREPARATION OF FLUORINE-RICH ORGANIC COMPOUNDS CONTAINING ONE OR TWO CARBON ATOMS

This invention relates to a process for the preparation of fluorine-rich organic compounds and more particularly, to a process for the catalytic disproportionation of aliphatic fluoro compounds of low fluorine content to produce aliphatic fluoro compounds of higher fluorine content.

Organic fluorine-rich compounds containing one or two carbon atoms are widely employed as refrigerants, solvents and intermediates for producing other valuable compounds. These fluorine-rich organic compounds have been industrially produced by treating halocarbons or partially halogenated hydrocarbons with anhydrous hydrogen fluoride in liquid or gas phase in the presence of catalysts such as antimony fluorochloride, chromium oxyfluoride, aluminum fluoride, etc., thereby substituting the halogen atom or atoms other than fluorine of the halocarbons or partially halogenated hydrocarbons with fluorine. However, the production of fluorine-rich organic compounds involves many disadvantages that the corrosive gas, i.e., anhydrous hydrogen fluoride, must be handled under severe reaction conditions and that since an excess of anhydrous hydrogen fluoride is used, the products obtained must be separated from the reaction system by washing, drying and other complicate procedures. It is thus highly desired to produce fluorine-rich organic compounds under less corrosive conditions in a simple and industrially advantageous manner.

For industrial production of fluorine-rich organic compounds, it is also known that partially or completely halogenated aliphatic fluoro compounds are convertible to more highly fluorinated compounds together with less fluorinated compounds by disproportionation in the presence of catalyst of a specific type without use of any anhydrous hydrogen fluoride.

The term "disproportionation" herein used is intended to imply the compensated reaction process as expressed, for example, by the following equilibrium reaction formulae when trichlorofluoromethane is used as starting halogenated aliphatic fluoro compound

As catalyst for the disproportionation reaction of partially or completely halogenated aliphatic fluoro compounds, there are usually employed aluminum chloride, aluminum bromide, and various types of aluminum fluorides obtained, for example, by treating these Fiedel-Crafts catalysts with anhydrous hydrogen fluoride. Further, there have been proposed a number of processes or catalysts for the disproportionation of partially or completely halogenated aliphatic fluoro compounds, including a catalyst obtained by treating activated alumina with lower aliphatic fluoro carbon compounds (Japanese Patent Publication No. 11605/1964), a chromium fluoride catalyst (Japanese Patent Publication No. 19568/1967), a process using trichromates (Japanese Laid-open Patent Application No. 134611/1974), a process using aluminum fluoride obtained by treating activated alumina with anhydrous hydrogen fluoride (Japanese Laid-open Patent Application No. 62194/1976), etc. However, all of these catalysts are unsatisfactory in yield and life time.

It is therefore an object of the present invention to provide a process for preparing partially or completely halogenated aliphatic fluoro compounds rich in fluorine from partially or completely halogenated aliphatic fluoro starting materials of lower fluorine content by use of a solid catalyst of a specific type.

It is another object of the present invention to provide a process using a catalyst for the disproportionation of aliphatic fluoro compounds which is high in catalytic and long in life.

It has been found that known aluminum compound catalysts for disproportionation are further improved in catalytic activity and life time by addition of a minor proportion of metal salts such as titanium or nickel salts. The present invention is based on the above finding and contemplates to provide a process for disproportionating a partially or completely halogenated fluoro derivative of methane containing not more than two fluorine atoms and at least one halogen atom other than fluorine, or a completely halogenated fluoro derivative of ethane containing from 2 to 4 halogen atoms other than fluorine and correspondingly from 4 to 2 fluorine atoms, the process comprising contacting the partially or completely halogenated fluoro derivative of methane or the completely halogenated fluoro derivative of ethane in gas phase and in a substantially moisture-free state under disproportionation conditions, with a catalyst substantially composed of from 0.1 to 5.0% by weight, as metal, of a metal salt selected from the group consisting of nickel (II) halides, titanium (III) chloride and titanium (III) fluoride and a balance of a compound selected from the group consisting of activated alumina, silica.alumina and aluminum fluoride.

The present invention is characterized by the catalyst of the specific type, by which the partially or completely halogenated fluoro compounds of low fluorine content can be converted to more highly fluorinated compounds in high yield and the high catalytic activity persists over a relatively long period of time unless the calalyst is not impaired, for example, by condensation of liquid material thereon. As will be understood from the above, the catalyst useful in the present invention is composed of a major proportion of an aluminum compound such as activated alumina, silica.alumina and/or aluminum fluoride and a minor proportion of a titanium or nickel salt. Of the aluminum compounds, aluminum fluoride and silica.alumina are most preferable due to high catalytic activity and long life when used in combination with the nickel or titanium salts. As well known in the art, aluminum fluorides are obtainable from a multiplicity of sources. In practice, any aluminum fluorides may be used, e.g., those obtained by treating activated alumina with anhydrous hydrogen fluoride or by heating the tetrafluoroaluminate at 400°–500° C to give β-aluminum fluoride. Aluminum fluoride, silica.aluminum or activated alumina available on the market is employable as one component of the catalyst used in the present invention.

The metal salts used in combination with the aluminum compound to form a catalyst for the disproportionation are nickel (II) halides such as nickel (II) chloride, nickel (II) iodide, nickel (II) bromide and nickel (II) fluoride and titanium (III) halides such as titanium (III) chloride and titanium (III) fluoride. The reason why the catalytic activity and durability of the catalyst substantially composed of the above-defined aluminum compound and the nickel or titanium salt are superior to known ones such as aluminum fluoride alone is not known. It is believed that the metal salt and the aluminum compound serve, in combination, as catalyst for the disproportionation since either of them does not exhibit by itself a catalytic activity and durability comparable to such combination.

In order to prepare the calalyst, it will suffice to dissolve the nickel or titanium salt in water, an aqueous hydrochloric acid or an alcohol, admix the aluminum compound such as activated alumina with the solution, under sufficient agitation, and remove the solvent by evaporation to dryness. If some moisture remains in the catalyst, the catalytic activity is lowered considerably, so that the evaporation must be effected fully by heating until no moisture is recognized, if possible, just before the reaction. It will be noted that the nickel (II) halides used to prepare the catalyst may be in either an anhydrous or hydrate form. That is, a number of known hydrated nickel (II) halides may be used as starting nickel (II) salt as well as anhydrous ones. The aluminum compound may be added to the solution in the form of powder, particles, granules, cylindrical or other suitable shapes. As a matter of course, the aluminum compound which has been immersed in the solution in the form of powder may be subsequently formed into a suitable shape for use as catalyst. Upon the shaping small amounts of binders may be added. When a binder is used, it should be removed by burning out under high temperature conditions in subsequent step.

The aluminum compound-added solution is needed to be agitated by a suitable means such as agitator for a time sufficient to impregnate the solid aluminum compound with the solution to a satisfactory extent. The nickel or titanium salt solution should have a concentration sufficient to ensure desposition of the salt on the aluminum compound in an amount defined hereinlater.

Then, the solvent is removed by heating under a normal or reduced pressure for several hours so that the nickel or titanium salt is firmly deposited as solid on the aluminum compound. The nickel or titanium salt should be deposited in an amount of from 0.1 to 5% by weight of a total amount of the catalyst when calculated as metal. Higher concentration may be used but does not appear to offer any advantages, while less concentration is disadvantageous in view of a material drop in catalytic activity. The catalyst thus prepared may be activated, prior to use, by merely heating in a stream of dry nitrogen or by treating with hydrogen fluoride gas at temperatures of 300° C to 400° C. In this connection, however, the catalyst will exhibit a satisfactory catalytic activity without resorting to such pretreatment. It will be noted that when the catalyst which is deposited with the nickel or titanium halides other the fluorides is treated with hydrogen fluoride gas, the nickel or titanium halides other than the fluorides may be converted to fluorides thereof.

The catalyst is generally used by packing it in a reaction tube, through which starting partially or completely halogenated aliphatic fluoro compounds are passed for disproportionation. The partially or completely halogenated fluoro compounds which can yield valuable fluorine-rich compounds when treated according to the process of the invention include completely halogenated fluoro derivatives of methane such as $CCl_3F$ and $CCl_2F_2$, partially halogenated fluoro derivatives of methane such as $CHCl_2F$, $CHClF_2$ and $CH_2ClF$, and completely halogenated fluoro derivatives of ethane such as $C_2Cl_2F_4$, $C_2Cl_3F_3$ and $C_2Cl_4F_2$.

The disproportionation reaction conditions, i.e., temperature and space velocity of starting gas, may vary, to some extent, depending on the particular starting material and also on the final product desired. The disproportionation process of the invention proceeds satisfactorily at temperatures ranging from 100° C to 600° C at space velocities ranging from 50 to 1000/hr, preferably 100 to 600/hr. The partially halogenated fluoro derivatives of methane have a tendency of being disproportionated at higher space velocity than the completely halogenated fluoro derivatives of methane and ethane when compared at the same level of reaction temperature. In this sense, the completely halogenated fluoro derivatives of methane may be disproportionated at higher space velocity than the ethane derivatives. In general, the space velocity at which the starting material vapor is passed through the reaction system depends on the temperature of the system. At lower temperatures, the space velocity is necessarily required to be smaller than at higher temperatures in order to attain the same level of yield, but industrially satisfactorily results may be obtained in the above-defined ranges of the space velocity and temperature.

The starting partially or completely halogenated fluoro derivatives of methane or ethane should be passed through the reaction in the vapor phase and in the substantially moisture-free state so as to avoid excessive deterioration of the catalyst by hydrolysis.

Optimum reaction conditions from an industrial viewpoint will be described with regard to typical partially and completely halogenated fluoro compounds such as $CHCl_2F$, $CCl_2F_2$ and $CCl_3F_3$.

Transformation of chlorodifluoromethane, $CHClF_2$, predominantly to $CHF_3$ is optimumly feasible in accordance with the process of the invention at a temperature of from 200° to 300° C at a space velocity 200–500/hr. For the purpose, $NiCl_2$-$\beta$-aluminum fluoride, $NiCl_2$-silica.alumina and $NiCl_2$- or $TiCl_3$-activated alumina which is subsequently treated for activation with anhydrous hydrogen fluoride at a temperature of, for example, from 300° to 400° C are preferably used. The above conditions may be likewise applied to the other partially halogenated fluoroderivatives, $CHCl_2F$ and $CH_2ClF$.

Optimum conditions for converting $CCl_2F_2$ to $CClF_3$ or $CCl_3F$ to $CCl_2F_2$ and $CClF_3$ are a temperature of from 200° to 300° C and space velocity of about 200/hr. High space velocity will lower the yield of the products desired.

Further, trichlorotrifluoroethane, $C_2Cl_3F_3$, is convertible to dichlorotetrafluoroethane in relatively high yield at about 300° C at a space velocity of about 140/hr, together with small amount of monochloropentafluoroethane. Higher temperature and lower space velocity may result in an increase of yield, but the increase is not so remarkable as to offer economical advantages. The disproportionation of the ethane derivative appears to be rather complicate and involves formation of several by-products such as $C_2Cl_4F_2$, $C_2Cl_5F$ and $CCl_2=CCl_2$.

As will be understood from the above, partially or completely halogenated aliphatic fluoro compounds of low fluorine content are conveniently converted to fluoro compounds richer in fluorine in accordance with the process of the invention.

Various reaction products obtained by the reaction may be readily recovered separately or in admixture by any known manner. In the practice of the invention, any suitable chamber or reactor tube constructed of inert materials such as glass may be employed for carrying out the process of the invention provided the reaction zone afforded is of sufficient length and cross-sectional area to accommodate a required amount of the catalyst system of the invention required for providing adequate gas content area, and at the same time afford sufficient free space for passage of the gaseous starting material at an economical rate of flow. Externally disposed reactor tube heating means such as steam jacket or electrical heaters may be supplied.

The present invention will be particularly illustrated by way of the following examples, which should not be construed as limiting thereto the present invention.

COMPARATIVE EXAMPLE 1

β-aluminum fluoride powder was obtained by thermal decomposition of ammonium tetrafluoroaluminate at 400°-450° C. The thus obtained powder was molded by use of a binder into a cylindrical shape with a diameter of 3-4 mm, 20 cc of which was packed in a 10 mm diameter reactor tube. The tube was then placed in a tubular furnace set at 300° C to sinter the moldings to remove the binder, to which chlorodifluoromethane was directly passed for activating the cylindrical aluminum fluoride. The preparation of the fluoride catalyst was regarded as being complete when no water was recognized at the outlet of the reactor tube. Thereafter, chlorodifluoromethane was fed at a space velocity of 200/hr for disproportionation at a temperature of 300° C. The gas product discharged from the reactor tube was passed into an air-cooled tube wherein part of products of high boiling points was removed by liquefaction. The resulting gaseous product was analyzed by a gas-chromatographic technique for determining the activity of the β-aluminum fluoride for the catalytic disproportionation reaction. The test results are shown in Table below.

| sampling time after commencement of feed of starting gaseous material (hrs) | production composition (wt%) | | | | catalytic activity* (%) |
|---|---|---|---|---|---|
| | $CHF_3$ | $CHClF_2$ | $CHCl_2H$ | $CHCl_3$ | |
| 6 | 1.1 | 93.8 | 0.3 | 4.8 | 1.2 |
| 22 | 37.1 | 49.4 | 8.0 | 5.5 | 42.9 |
| 46 | 25.8 | 59.9 | 7.4 | 6.9 | 30.1 |

Note:
The catalytic activity for chlorodifluoromethane used as starting material was defined as follows:

$$\text{Catalytic activity for chlorodifluoromethane (\%)} = \frac{\text{produced trifluoromethane (wt\%)}}{\text{produced trifluoromethane (wt\%)} + \text{residual chlorodifluoromethane (wt\%)}} \times 100$$

The catalytic activity for dichlorodifluoromethane which is used as starting material in Examples appearing hereinlater is also determined as follows:

$$\text{Catalytic activity for dichlorodifluoromethane (\%)} = \frac{\text{produced chlorotrifluoromethane (wt\%)}}{\text{produced chlorotrifluoromethane (wt\%)} + \text{residual chlorodifluoromethane (wt\%)}} \times 100$$

When the above process was repeated using a reaction temperature of 200° C, 99.8% of $CHClF_2$ was found to be recovered 40 hours after commencement of the reaction.

From the above, it will be understood that the β-$AlF_3$ catalyst is poor in catalytic activity and also in lifetime when $CHCl_2F$ is used as starting material.

EXAMPLES 1-4

0.607 g of $NiCl_2.6H_2O$ of guaranteed grade was dissolved in 50 ml of methanol, to which was added 30 g of the β-aluminum fluoride of the cylindrical form as prepared in Comparative Example 1. Then, the methanol was removed under reduced pressure by means of a rotary evaporator to obtain a 0.5 wt% $NiCl_2$-on-β-aluminum fluoride catalyst when calculated as Ni. The procedure of Comparative Example 1 was repeated using 20 cc of the catalyst, reaction temperatures ranging from 100° to 200° C and a space velocity of 200/hr, with the following test results.

| Example No. | reaction temperature (° C) | time sampled after commencement of reaction (hrs) | product composition (wt%) | | | | catalytic activity |
|---|---|---|---|---|---|---|---|
| | | | $CHF_3$ | $CHClF_2$ | $CHCl_2F$ | $CHCl_3$ | |
| 1 | 200 | 2.5 | 75.2 | 10.2 | 5.3 | 9.3 | 88.0 |
| 2 | 200 | 18.0 | 86.0 | 4.6 | 3.3 | 6.1 | 94.5 |
| 3 | 150 | 20.0 | 49.8 | 33.0 | 5.4 | 11.9 | 60.1 |
| 4 | 100 | 23.0 | 23.9 | 62.8 | 3.2 | 10.1 | 27.6 |

EXAMPLES 5-6

Pellets of activated alumina (with a diameter of 6 mm and a thickness of 3mm, product of Sumitomo Chem. Co., KAT-6) were immersed in an aqueous 5 wt% titanium trichloride solution for a time under agitation and removed from the solution to allow 2.5% by weight, as Ti, of $TiCl_3$ to be deposited on the pellets, followed by drying at 130° C for 6 hours to obtain 2.5 wt% $TiCl_3$-on-activated alumina pellets when calculated at Ti. The pellets were then packed in a nickel tube reactor with an inner diameter of 20 mm and a length of 400 mm and treated for activation with anhydrous hydrogen fluoride at 350° C to prepare a $Ti^{3+}$-on-aluminum fluoride catalyst ($TiCl_3$ seems to be converted to $TiF_3$, but not same manner as in Examples 5 and 6. A gaseous product was sampled 2 hrs after commencement of the reaction and subjected to a gas-chromatographic analysis. The test results are also shown in the Table.

| Example No. | kind of catalyst | reaction temperature (° C) | product composition (wt%) | | | | catalytic activity (%) |
|---|---|---|---|---|---|---|---|
| | | | $ClF_3$ | $CCl_2F_2$ | $CCl_3F$ | $CCl_4$ | |
| 7 | $Ti^{3+}$-$AlF_3$ | 200 | 61.3 | 15.4 | 8.34 | 15.2 | 79.9 |
| 8 | $Ti^{3+}$-$AlF_3$ | 300 | 64.1 | 12.8 | 7.09 | 16.0 | 83.4 |
| 9 | $Ni^{2+}$-$AlF_3$ | 200 | 58.4 | 13.6 | 7.09 | 21.0 | 81.1 |
| 10 | $Ni^{2+}$-$AlF_3$ | 300 | 61.9 | 13.7 | 7.71 | 16.7 | 81.9 | confirmed, so that $TiCl_3$ treated with anhydrous hydrogen fluoride is expressed merely in terms of $Ti^{3+}$ herein and whenever it appears hereinlater. This is also applied to $NiCl_2$ or $CrCl_3$ treated with anhydrous hydrogen fluoride.) 20 cc of the catalyst was packed in a 10 mm diameter glass reactor tube, through which chlorodifluoromethane was passed for disproportionation at a temperature of 200° C at a space velocity of 200/hr over 2 hours. The gaseous product was directly sampled and subjected to a gas-chromatographic analysis.

Further, the above process was repeated using an aqueous 5 wt% $NiCl_2.6H_2O$ solution instead of the aqueous titanium trichloride solution thereby obtaining a 2.5 wt% $Ni^{2+}$-on-aluminum fluoride catalyst. Then, the disproportionation of chlorodifluoromethane was conducted by use of the catalyst in the same manner as described above. The test results are shown in Table below.

| Example No. | kind of catalyst | product composition (wt%) | | | | catalytic activity |
|---|---|---|---|---|---|---|
| | | $CHF_3$ | $CHClF_2$ | $CHCl_2F$ | $CHCl_3$ | |
| 5 | $Ti^{3+}$ — $AlF_3$ | 67.2 | 2.69 | 2.54 | 27.5 | 96.2 |
| 6 | $Ni^{2+}$ — $AF_3$ | 58.8 | 3.00 | 2.82 | 35.4 | 95.1 |

COMPARATIVE EXAMPLE 2

100 cc of activated alumina powder was treated with anhydrous hydrogen fluoride at 350° C to convert the activated alumina to aluminum fluoride.

While, the procedure of Examples 5 and 6 was repeated using an aqueous 5 wt% $CrCl_3.6H_2O$ solution instead of the aqueous 5 wt% $TiCl_3$ or $NiCl_2.6H_2O$ solution to prepare a 5 wt% $Cr^{3+}$-on-aluminum fluoride catalyst.

The two kinds of the catalysts were, each used for the disproportionation of chlorodifluoromethane in the gas phase at a temperature of 200° C and at a space velocity of 200/hr.

The product obtained 2 hours after commencement of the reaction, was analyzed by a gas-chromatograhic technique, with the following results.

| kind of catalyst | product composition (wt%) | | | | catalytic activity (%) |
|---|---|---|---|---|---|
| | $CHF_3$ | $CHClF_2$ | $CHCl_2F$ | $CHCl_3$ | |
| $AlF_3$ | 62.6 | 3.90 | 3.80 | 29.5 | 94.1 |
| $Cr^{3+}$—$AlF_3$ | 44.8 | 29.8 | 3.10 | 22.3 | 60.0 |

EXAMPLES 7-10

The same kinds of the catalysts as in Examples 5 and 6 were used, respectively, for the disproportionation of dichlorodifluoromethane at a space velocity of 200/hr at different temperatures shown in Table below in the

EXAMPLE 11

100 cc of activated alumina granules were immersed in 150 cc of an aqueous $TiCl_3$ solution which was prepared by adding 50 cc of pure water to 100 cc of an aqeuous 20% $TiCl_3$ solution for 6 hours, followed by removing the solution and drying at 100° C for 6 hours to obtain a 3 wt% $TiCl_3$-on-activated alumina catalyst when calculated as metal. The thus obtained catalyst was packed in a nickel reactor tube, through which anhydrous hydrogen fluoride was continuously passed at 400° C until no moisture was recognized in the exit gas. Thereafter, nitrogen gas was fed into the reactor tube to purge remaining anhydrous hydrogen fluoride. The reactor tube was set at 300° C and then trichlorotrifluoroethane was fed into the tube at a space velocity of 140/hr. The resulting gaseous produce was sampled 1 hour after commencement of the disproportionation and analyzed by a gas-chromatograhic technique with the following results.

| Product Composition | |
|---|---|
| $C_2ClF_5$ | 6.0 mol% |
| $C_2Cl_2F_4$ | 37.6 mol% |
| $C_2Cl_3F_3$ | 47.4 mol% |
| $C_2Cl_4F_2$ | 7.1 mol% |
| $C_2Cl_5F$ | 1.3 mol% |
| $CCl_2=CCl_2$ | 0.6 mol% |

EXAMPLE 12

48.6 g of $NiCl_2.6H_2O$, 400 g of β-aluminum fluoride powder and 500 ml of methanol were introduced into a 2 l flask equipped with a reflux condenser and an agitator and sufficiently agitated for 1.5 hours under such conditions as to allow the methanol to reflux. The methanol was removed by heating and the remaining powder was vacuum dried and reduced to finer powder by means of a ball mill. The finder powder was added with a small amount of a binder and shaped into a cylindrical form of 3-4 mm in diameter by use of a tablet machine to obtain a 3 wt%, as metal, $NiCl_2$-β-$AlF_3$, catalyst. The catalyst was packed in a reactor tube and calcined in a stream of nitrogen at 350° C for 2 hours. Thereafter, the catalyst was cooled down to 200° C and contacted with chlorodifluoromethane at a space velocity of 200/hr while maintaining the temperature of 200° C. The gaseous product obtained 1 hour after passage of chlorodifluoromethane was analyzed by a gas-chromatographic technique with the following result:

| | |
|---|---|
| $CHF_3$ | 62.2 wt% |
| $CHClF_2$ | 3.69 " |
| $CHCl_2F$ | 3.91 " |
| $CHCl_3$ | 30.2 " |
| catalytic activity | 94.4 % |

EXAMPLES 13 – 16

The procedure of Examples 1 – 4 was repeated using silica.alumina catalyst (available from Nikki Chem. Co., under the designation N632-L), thereby obtaining a 0.5 wt% $NiCl_2$-on-silica.alumina catalyst when calculated as metal. The catalyst was packed in a reactor tube, through which chlorodifluoromethane was passed under different reaction conditions shown in Table below. Predetermined periods of time after the passage, the resulting gaseous products were, respectively, sampled and washed with water and subjected to a gas-chromatographic analysis with the following results.

For comparative purpose, the above procedure was repeated using the silica.alumina catalyst alone.

of a metal salt selected from the group consisting of nickel (II) halides, titanium (III) chloride and titanium (III) fluoride and a balance of a compound selected from the group consisting of activated alumina, silica.alumina and aluminum fluoride.

2. A process according to claim 1, wherein said derivative of methane is $CHCl_2F$ or $CHClF_2$, and the disproportionation is conducted at a temperature of from 200° to 300° C at a space velocity of from 200 to 500/hr.

3. A process according to claim 1, wherein said derivative of methane is chlorodifluoromethane, $CHClF_2$, the disproportionation is conducted at a temperature of from 200° to 300° C at a space velocity of from 200 to 500/hr, and said metal salt is nickel (II) chloride and said compound is β-aluminum fluoride.

4. A process according to claim 1, wherein said derivative of methane is chlorodifluoromethane, $CHClF_2$, the disproportionation is conducted at a temperature of from 200° to 300° C at a space velocity of from 200 to 500/hr, and said metal salt is nickel (II) chloride and said compound is silica.alumina.

5. A process according to claim 1, wherein said derivative of methane is chlorodifluoromethane, $CHCl_2F$, the disproportionation is conducted at a temperature of

| Example No. | time sampled after commencement of reaction (hrs) | reaction temperature (° C) | space velocity (/hr) | reaction product (wt%) | | | | catalytic activity (%) |
|---|---|---|---|---|---|---|---|---|
| | | | | $CHF_3$ | $CHClF_2$ | $CHCl_2F$ | $CHCl_3$ | |
| 13 | 7 | 300 | 200 | 87.7 | 4.1 | 2.5 | 5.7 | 95.5 |
| 14 | 9 | 200 | 200 | 85.8 | 2.6 | 2.5 | 9.1 | 97.1 |
| 15 | 13 | 200 | 300 | 87.1 | 2.4 | 2.0 | 8.5 | 97.3 |
| 16 | 15 | 200 | 500 | 86.3 | 2.8 | 2.0 | 8.9 | 96.9 |
| for comparison | 7 | 300 | 200 | 84.4 | 4.9 | 3.6 | 7.1 | 94.5 |

What is claimed is:

1. A process for disproportionating a partially or completely halogenated fluoro derivative of methane containing not more than two fluorine atoms and at least one halogen atom other than fluorine or a completely halogenated fluoro derivative of ethane containing from 2 to 4 halogen atoms other than fluorine and correspondingly from 4 to 2 fluorine atoms, the process comprising contacting said derivative of methane or said derivative of ethane in gas phase and in a substantially moisture-free state under disproportionation conditions of a temperature of 100 to 600° C and a space velocity of from 50 to 1000/hr, with a catalyst substantially composed of from 0.1 to 5.0% by weight, as metal, from 200° to 300° C at a space velocity of from 200 to 500/hr, and said catalyst is $NiCl_2$- or $TiCl_3$-activated alumina which is subsequently treated for activation with anhydrous hydrogen fluoride at a temperature of from 300° to 400° C.

6. A process according to claim 1, wherein said derivative of methane is dichlorodifluoromethane, the disproportionation is conducted at a temperature of from 200° to 300° C at a space velocity of about 200/hr.

7. A process according to claim 1, wherein said derivative of ethane is trichlorotrifluoroethane and the disproportionation is conducted at a temperature of about 300° C and at a space velocity of about 140/hr.

* * * * *